United States Patent [19]
Villari

[11] 4,366,836
[45] Jan. 4, 1983

[54] VALVED VENT FOR A LIQUID DRAINAGE SYSTEM

[75] Inventor: Frank K. Villari, Oak Park, Ill.

[73] Assignee: The Kendall Company, Boston, Mass.

[21] Appl. No.: 187,910

[22] Filed: Sep. 17, 1980

[51] Int. Cl.³ .............................................. F16K 31/00
[52] U.S. Cl. .................................... 137/550; 251/339; 251/342; 128/760
[58] Field of Search ...................... 251/339, 342, 354; 137/550; 128/760, 761, 767, 771

[56] References Cited

U.S. PATENT DOCUMENTS

| | | | |
|---|---|---|---|
| 2,106,671 | 1/1938 | Watson | 251/339 X |
| 3,530,928 | 9/1970 | Swinney | 251/342 X |
| 3,683,894 | 8/1972 | Villari | 128/771 |
| 3,831,453 | 8/1974 | McWhorter | 73/427 |
| 3,918,483 | 11/1975 | Van Leeuwer | 137/550 |
| 4,116,227 | 9/1978 | Eisenberg et al. | 128/768 |
| 4,126,558 | 11/1978 | Luceyk | 210/429 |

Primary Examiner—A. Michael Chambers
Attorney, Agent, or Firm—Powell L. Sprunger

[57] ABSTRACT

A valved vent for a liquid drainage system comprising, a receptacle having a chamber to receive liquid, and a filter pervious to air and substantially impervious to the passage of bacteria, with the filter communicating with the atmosphere. The vent has a valve communicating between an upper portion of the chamber and the filter. The valve may be selectively opened to permit passage of air between the atmosphere and the chamber through the filter, and may be selectively closed to prevent passage of liquid from the chamber against the filter.

9 Claims, 4 Drawing Figures

VALVED VENT FOR A LIQUID DRAINAGE SYSTEM

BACKGROUND OF THE INVENTION

The present invention relates to liquid drainage systems.

Before the present invention, an assortment of urine meters have been proposed to collect urine which drains through a catheter and drainage tube from a patient. The urine meters normally comprise a receptacle having a chamber to receive liquid from the drainage tube, and a container having a cavity. Provision is made for emptying the liquid from the receptacle chamber into the container cavity for retention therein. During the emptying procedure, a negative pressure is created in the receptacle chamber which impedes passage of liquid from the receptacle to the container. Thus, vents have been placed on the receptacle to permit passage of air from the atmosphere to the chamber in order to alleviate the negative pressure in the receptacle. Such vents have been provided with a filter in order to remove bacteria from the air which passes into the chamber, and thus prevent contamination of the system. However, during use of the device urine from the chamber may contact the receptacle filter, and it has been found that repeated contact by urine against the filter may cause closure of the filter. Thus, the vent on the receptacle may be rendered inoperative in that it no longer permits passage of air through the filter. As a result, a negative pressure is created in the receptacle when attempting to empty the receptacle into the container, thus preventing passage of liquid from the receptacle and also rendering the urine meter inoperative.

SUMMARY OF THE INVENTION

The principal feature of the present invention is the provision of improved vent means for a liquid drainage system.

The drainage system has a receptacle having a chamber to receive liquid, and the vent means has a filter pervious to air and substantially impervious to the passage to bacteria, with the filter communicating with the atmosphere. The vent means has valve means communicating between an upper portion of the chamber and the filter.

A feature of the present invention is that the valve means is normally closed to prevent contact of liquid from the chamber against the filter.

Thus, another feature of the invention is that the valve means prevents damage to the filter by the liquid during use of the device.

Yet another feature of the invention is that the valve means may be selectively opened to permit passage of air between the atmosphere and the chamber through the filter.

Accordingly, a feature of the present invention is that a negative pressure may be alleviated in the receptacle chamber by actuation of the valve means.

Further features will become more fully apparent in the following description of the embodiments of this invention and from the appended claims.

DESCRIPTION OF THE PREFERRED EMBODIMENTS

Figure 1:
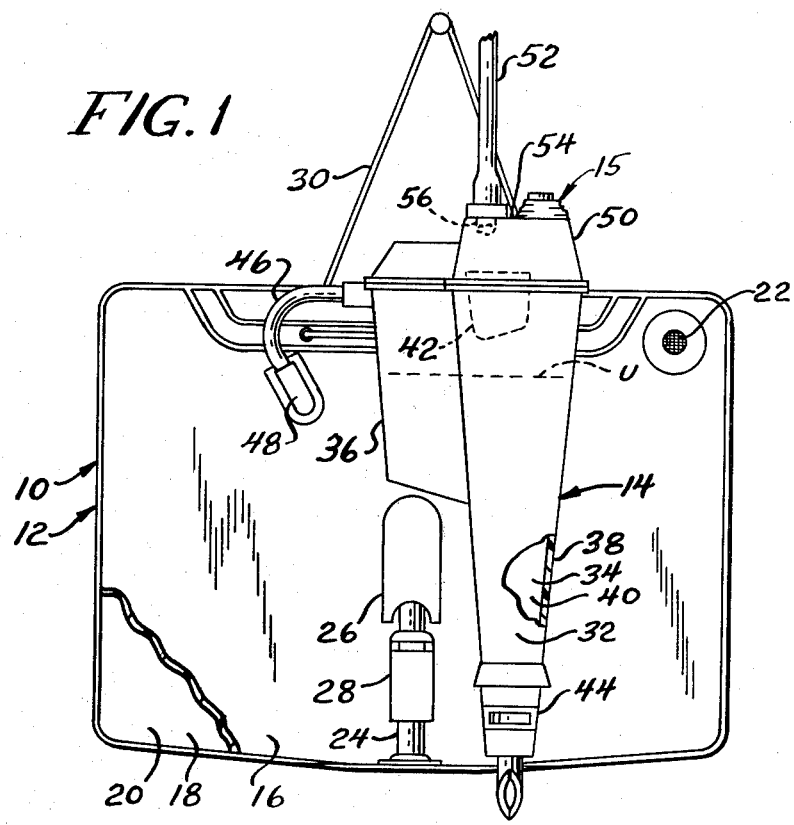
FIG. 1 is a fragmentary front plan view, partly broken away, of a liquid drainage system having vent means of the present invention.

Referring now to FIG. 1, there is shown a urine meter generally designated 10 in a liquid drainage system having a container 12, a receptacle 14, and a vent 15 in an upper portion of the receptacle 14. The container 12 has a front wall 16 and a rear wall 18 of flexible material, such as a suitable plastic, being joined together around the periphery thereof and defining a cavity 20 between the front and rear walls 16 and 18. The front wall 16 of the container 12 has a vent 22 with a bacterial filter of known type communicating with the container cavity 20. The container 12 has a tubular section 24 communicating with a lower portion of the cavity 20, and having an outer end removably received in a pocket 26, with the tubular section 24 having a releasable clamp 28 on the tubular section. Thus, when it is desirable to drain urine from the container 12, the tubular section 24 is removed from the pocket 26, and the clamp 28 is released to permit passage of urine through the tubular section 24. The container 12 also has a string 30 attached to an upper portion of the container 12 to permit hanging of the urine meter 10 from a suitable object during use.

The receptacle 14 has a front wall 32, a rear wall 34, and a pair of side walls 36 and 38 defining a chamber 40 in the receptacle 14. The receptacle 14 has a hook 42 extending from the rear wall 34 and spaced from the rear wall 34 to receive an upper portion of the container 12 in order to support the receptacle 14 on the upper portion of the container 12. The receptacle 14 has a lower valve 44 to permit draining of urine when desired from the receptacle chamber 40 to obtain a specimen of urine. The urine meter 10 has a flexible tube 46 having one end connected to the receptacle 14 adjacent the side wall 36 such that it communicates with an upper portion of the chamber 40, and the other end of the tube 46 is attached by a connector 48 to an upper portion of the container 12 on the front wall 16, such that the tube 46 communicates with an upper portion of the cavity 20. Thus, the tube 46 communicates between an upper portion of the chamber 40 and an upper portion of the cavity 20 for a purpose which will be described below.

As shown, the receptacle 14 has a raised portion 50 adjacent an upper end of the receptacle 14. The urine meter 10 has a drainage tube 52 for draining urine from the patient, with a downstream end of the drainage tube 52 extending through an upper wall 54 of the raised portion 50 into the receptacle 14 to define a drip tube 56 inside the receptacle 14. The receptacle 14 has the vent 15 attached to the upper wall 54.

Figure 2:
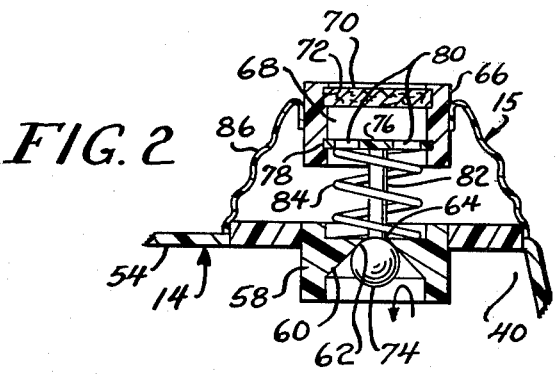
FIG. 2 is a fragmentary sectional view of the vent means in a closed configuration.

With reference to FIG. 2, the receptacle 15 has a tubular section 58 attached to the upper wall 54, with the tubular section 58 having an inner tapered flange 60 which defines a conical valve seat 62 surrounding an opening 64 which communicates with the receptacle chamber 40. The vent 15 has a housing 66 comprising a tubular section which defines a lumen 68. The vent 15 has a circular filter 70 of known type which is pervious to the passage of air, but is substantially impervious to the passage of bacteria. As shown, the housing 66 has a recess 72 to retain the filter 70 in place in the lumen 68, with the filter 70 communicating with the atmosphere.

The vent 15 has a valve element 74 comprising a spherical ball which has a larger diameter than the diameter of the opening 64. The housing 66 has a plate 76 retained by a recess 78 in the housing 66, such that the plate 76 is positioned in the lumen 68 of the housing 66. As shown, the plate 76 has a plurality of apertures 80 extending through the plate 76 to permit passage of air through the plate 76. The vent 15 has a rod 82 connected between a central portion of the plate 76 and the valve element 74, with the rod 82 passing through the opening 64. The rod 82 has a smaller diameter than the diameter of the opening 64 in order to permit movement of the rod 82 through the opening 64.

The vent 15 has a helical spring 84 extending between the plate 76 and the flange 60 such that the spring 84 biases the housing 66 away from the receptacle 14. Thus, the spring 84 biases the valve element 74 against the valve seat 62, such that the valve element 74 normally sealingly engages against the valve seat 62. In this manner, the valve of the vent 15 comprising the valve element 74 and the valve seat 62 is normally maintained in a closed configuration. The vent 15 also has a flexible wall 86 of suitable material, such as a flexible plastic, extending peripherally around the housing 66 and extending between the housing 66 and the upper wall 54 of the receptacle 14, such that the wall 86 closes the vent 15 intermediate the housing 66 and the receptacle 14.

As previously discussed, the valve of the vent 15 is maintained in a normally closed configuration, with the valve element 74 sealingly engaging against the valve seat 62. Thus, the normally closed valve prevents passage of urine from the receptacle chamber 40 through the opening 64 and against the filter 70. In this manner, the valve of the vent 15 normally prevents contact of urine against the filter 70 in order to prevent degradation and closure of the filter 70 otherwise caused by the contact of urine against the filter 70.

Figure 4:
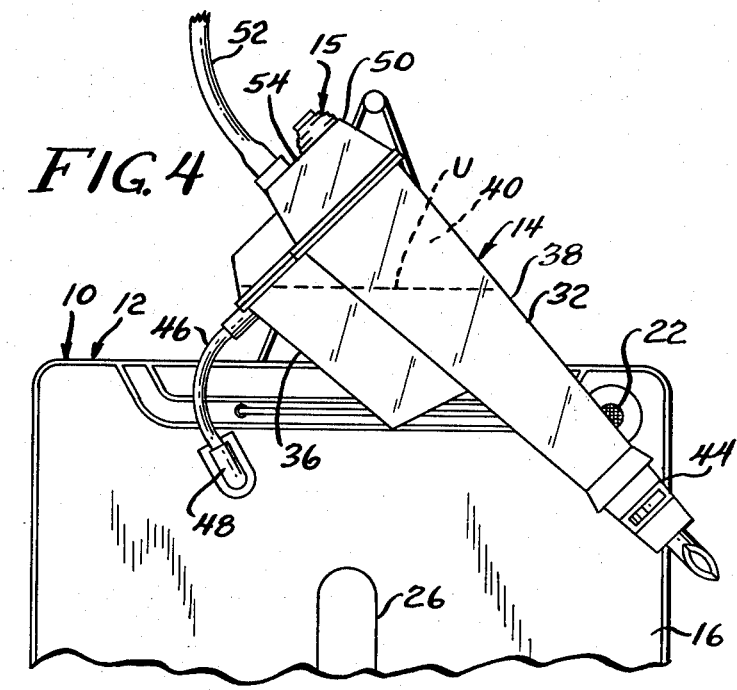
FIG. 4 is a fragmentary front plan view illustrating a receptacle of the drainage system being tilted to pass urine into a container of the drainage system.
Figure 3:
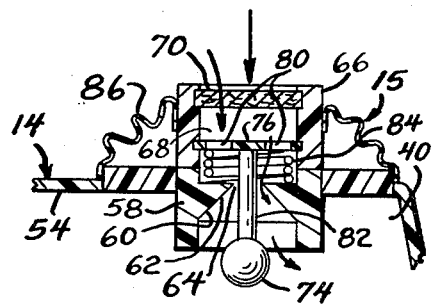
FIG. 3 is a fragmentary sectional view of the vent means in an open configuration.

With reference to FIG. 4, when it is desired to empty urine U from the receptacle 14 into the container 12, the receptacle 14 is lifted and tilted to permit passage of the urine U through the tube 46 and connector 48 into the cavity 20 of the container 12. However, at this time, a negative pressure is created in the upper portion of the receptacle chamber 40. With reference to FIG. 3, the vent housing 66 may be pressed toward the receptacle 14, such that the plate 76 and rod 82 move the valve element 74 away from the valve seat 62. In this open configuration of the valve, air is permitted to pass through the filter 70, the apertures 80 of the plate 76, and through the opening 64 into the chamber 40 of the receptacle 14. In this manner, the negative pressure in the receptacle chamber 40 is alleviated by the passage of filtered air into the receptacle chamber 40. During this time, the flexible wall 86 prevents the passage of air through the side of the vent 15, and limits the passage of air from the atmosphere through the filter 70 in order to assure that all the air passing into the receptacle has been filtered for bacteria.

Thus, in accordance with the present invention, the valve of the vent 15 is normally maintained in a first closed position with the valve element 74 sealingly engaged against the valve seat 62. However, the vent housing 66 may be pressed in order to move the valve to a second open position, thus permitting passage of air through the filter 70 and the valve to alleviate negative pressure in the chamber 40 of the receptacle 14. When the housing 66 is again released, the spring 84 biases the housing 66 away from the receptacle 14 to the normal first position of the valve, with the valve element 74 sealingly engaged against the seat 62 in order to again close the valve and prevent contact by urine against the filter 70. Thus, when it is desired to empty urine U from the receptacle 14 into the container 12, the valve of the vent 15 may be actuated to alleviate negative pressure in the receptacle chamber 40. When the emptying procedure has been completed, the housing 66 of the vent 15 may be released in order to again close the valve of the vent 15.

The foregoing detailed description is given for clearness of understanding only, and no unnecessary limitations should be understood therefrom, as modifications will be obvious to those skilled in the art.

I claim:

1. Valved vent means for a liquid drainage system, comprising:
   a receptacle having a chamber to receive liquid;
   a filter pervious to air and substantially impervious to passage of bacteria;
   a movable housing for retaining said filter, said housing including means for retaining said filter within an upper end of said housing thus to expose an exterior surface of said filter to atmosphere, in an unobstructed manner;
   a valve seat in an upper portion of the receptacle surrounding an opening communicating with said chamber, said seat being located substantially beneath said housing;
   a valve element for sealing engagement with said seat;
   means interconnecting said valve element with said housing, through said opening and substantially entirely beneath said filter, whereby upon depression of said movable housing, said valve element is moved away from said seat thus to vent said chamber through said filter, said filter being located at said upper housing end, remote from said valve element, said valve seat and said means interconnecting said valve element and housing, to minimize the possibility of contact of liquid within said chamber with said filter during venting of said chamber; and
   means for biasing the housing away from the receptacle and the valve element against said seat, whereby passage of liquid from the chamber against the filter is effectively prevented.

2. The valved vent means of claim 1 wherein the biasing means comprises a helical spring.

3. The valved vent means of claim 1 including flexible wall means extending peripherally around the housing and between the housing and receptacle.

4. The valved vent means of claim 1 including means for closing the vent means to the atmosphere intermediate the housing and receptacle.

5. The valved vent means of claim 1 wherein the housing comprises a tubular section having a lumen to receive said filter.

6. The valved vent means of claim 1 wherein said valve element comprises a spherical ball having a larger diameter than the diameter of said opening.

7. The valved vent means of claim 1 wherein the connecting means comprises a plate of the housing and having opening means to permit passage of air therethrough, and a rod extending between said plate and said valve element through said opening, said rod having a smaller diameter than the diameter of said opening to permit movement of the rod through said opening.

8. The valved vent means of claim 1 further comprising a container having a cavity, and means communicating between said chamber and said cavity to permit passage of liquid from the receptacle to the container.

9. Valved vent means for a liquid drainage system, comprising:
- a receptacle having a chamber to receive liquid;
- a filter pervious to air and substantially impervious to passage of bacteria;
- a movable housing comprising a tubular section defining a lumen to receive the filter with the filter communicating with the atmosphere, said housing having a plate in said lumen having opening means to permit passage of air therethrough;
- a valve seat in an upper portion of the receptacle surrounding an opening communicating with said chamber, said seat being located substantially beneath said housing;
- a valve element having larger dimensions than said opening to sealingly engage against said seat;
- a rod connecting said housing plate to said valve element through said opening, said rod having smaller dimensions than said opening to permit movement of said rod through said opening, said plate and rod being located substantially entirely beneath said filter;
- a helical spring surrounding said rod and extending between said housing and the receptacle, said spring biasing the housing away from the receptacle and biasing the valve element against the seat; and
- a flexible wall extending between the housing and receptacle peripherally around the housing, with said wall closing the vent means to the atmosphere intermediate the housing and receptacle, said filter being disposed substantially entirely above said plate whereby upon depression of said housing, thus to move said valve element away from said seat and vent said chamber to atmosphere through said filter, the possibility of liquid within said chamber coming into contact with said filter is minimized due to the location of said filter remote from said valve seat, said plate, valve element, rod and spring, all of which are located between said filter and said valve seat.

* * * * *